US00PP37430P2

(12) United States Plant Patent
van Swieten

(10) Patent No.: US PP37,430 P2
(45) Date of Patent: May 19, 2026

(54) ***PHALAENOPSIS* PLANT NAMED 'PHA801803'**

(50) Latin Name: *Phalaenopsis hybrida*
Varietal Denomination: PHA801803

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/329,292

(22) Filed: Sep. 15, 2025

(51) Int. Cl.
*A01H 6/62* (2018.01)
*A01H 5/02* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'PHA801803', characterized by its upright plant habit; medium to tall in height; moderately vigorous to vigorous growth habit and moderate to rapid growth rate; strong flowering stems; freely flowering habit with typically three inflorescences developing per plant, each inflorescence with numerous flowers; medium to broad white-colored flowers; and good postproduction longevity.

2 Drawing Sheets

Figure 1:
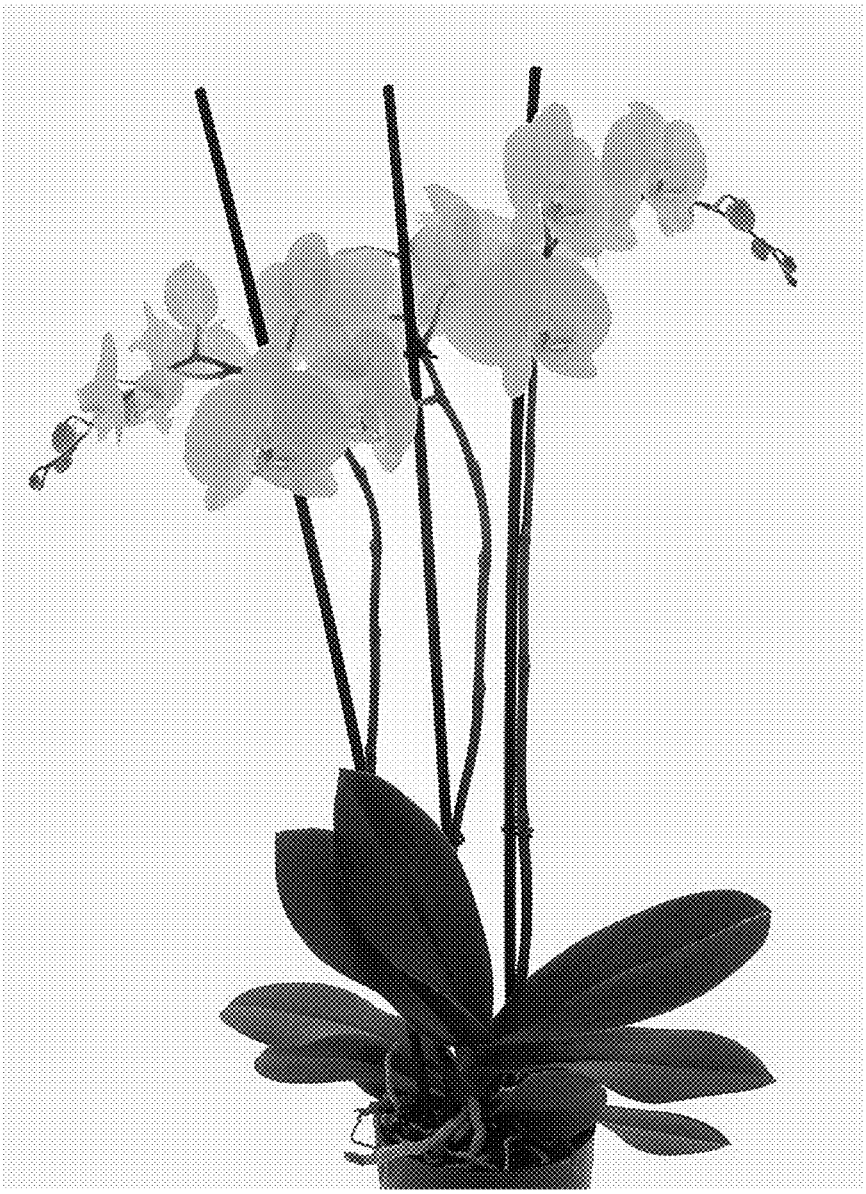

Botanical designation: *Phalaenopsis hybrida.*
Cultivar denomination: 'PHA801803'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Dec. 30, 2024, application number 2024/3265. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA801803'.

The new *Phalaenopsis* plant is a product of a planned breeding program conducted by the Inventor in Bleiswijk, The Netherlands. The objective of the breeding program is to develop new freely flowering *Phalaenopsis* plants with white-colored flowers.

The new *Phalaenopsis* plant originated from a cross-pollination in June, 2017 in Bleiswijk, The Netherlands of *Phalaenopsis hybrida* 'PHALHORDIN', disclosed in U.S. Plant Pat. No. 33,096, as the female, or seed, parent with *Phalaenopsis hybrida* 'PHALHETWER', disclosed in U.S. Plant Pat. No. 33,526, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in March, 2020.

Asexual reproduction of the new *Phalaenopsis* plant by in vitro meristem propagation in a controlled environment in Bleiswijk, The Netherlands since March, 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA801803'. These characteristics in combination distinguish 'PHA801803' as a new and distinct *Phalaenopsis* plant:

1. Upright plant habit; medium to tall in height.
2. Moderately vigorous to vigorous growth habit and moderate to rapid growth rate.
3. Strong flowering stems.
4. Freely flowering habit with typically three inflorescences developing per plant, each inflorescence with numerous flowers.
5. Medium to broad white-colored flowers.
6. Good postproduction longevity.

Plants of the new *Phalaenopsis* can be compared to plants of the female parent, 'PHALHORDIN'. Plants of the new *Phalaenopsis* differ primarily from plants of 'PHALHORDIN' in the following characteristics:

1. Leaves of plants of the new *Phalaenopsis* are semi-erect to horizontal in aspect whereas leaves of plants of 'PHALHORDIN' are horizontal to semi-drooping in aspect.

2. The petal apices of plants of the new *Phalaenopsis* are rounded to shallowly retuse whereas the petal apices of plants of 'PHALHORDIN' are emarginate.

Plants of the new *Phalaenopsis* can be compared to plants of the male parent, 'PHALHETWER'. Plants of the new *Phalaenopsis* differ primarily from plants of 'PHALHETWER' in the following characteristics:

1. Flowers of plants of the new *Phalaenopsis* are not as broad as flowers of plants of 'PHALHETWER'.
2. Dorsal sepals of plants of the new *Phalaenopsis* are shorter than dorsal sepals of plants of 'PHALHETWER'.

Plants of the new *Phalaenopsis* can be compared to plants of *Phalaenopsis hybrida* 'PHA773779', disclosed in U.S. Plant Pat. No. 35,381. In side-by-side comparisons, plants of the new *Phalaenopsis* differ primarily from plants of 'PHA773779' in the following characteristics:

1. Leaves of plants of the new *Phalaenopsis* are semi-erect to horizontal in aspect whereas leaves of plants of 'PHA773779' are horizontal to semi-drooping in aspect.
2. Dorsal sepals of plants of the new *Phalaenopsis* are shorter than dorsal sepals of plants of 'PHA773779'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA801803' grown in a container.

Figure 2:
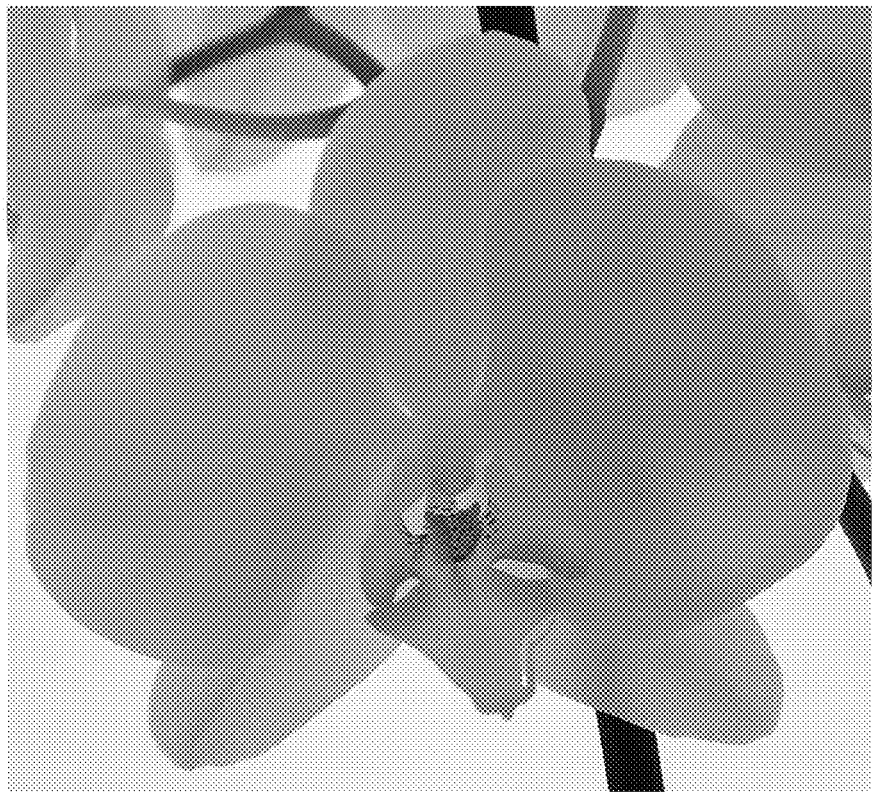

The photograph on the second sheet (FIG. 2) is a close-up view of a typical flower of 'PHA801803'.

DETAILED BOTANICAL DESCRIPTION

The aforementioned photographs and following observations and measurements describe plants grown during the winter in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA801803'.

Parentage:

*Female, or seed, parent.*—*Phalaenopsis hybrida* 'PHALHORDIN', disclosed in U.S. Plant Pat. No. 33,096.

*Male, or pollen, parent.*—*Phalaenopsis hybrida* 'PHALHETWER', disclosed in U.S. Plant Pat. No. 33,526.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically light green in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit; medium to tall in height; typically three inflorescences developing per plant, each inflorescence with numerous flowers; monopodial; moderately vigorous to vigorous growth habit and moderate to rapid growth rate.

*Plant height, substrate level to top of foliar plane.*—About 18 cm.

*Plant height, substrate level to top of floral plane.*—About 56.7 cm.

*Plant diameter or spread.*—About 37 cm.

Leaf description:

*Arrangement and quantity.*—Distichous, simple; sessile; about six to eight fully-developed leaves per plant.

*Length.*—About 20.1 cm.

*Width.*—About 6.5 cm.

*Aspect.*—Semi-erect to horizontal.

*Shape.*—Narrowly elliptic to narrowly elliptic-oblong and narrowly obovate-elliptic; slightly carinate.

*Apex.*—Unequal acute.

*Base.*—Sheathing. Sheath length: About 2.1 cm. Sheath width: About 1.6 cm. Sheath color: Close to 143B; distal margins, close to 143A.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Close to NN137A; narrow marginal edges, close to 145A. Developing leaves, lower surface: Close to 146A; narrow marginal edges, close to 145A. Fully expanded leaves, upper surface: Close to 137B; narrow marginal edges, close to 145B and 145C; venation, close to NN137A. Fully expanded leaves, lower surface: Close to a blend of 146B and 147B; narrow marginal edges, close to 145B; venation, close to 144B.

Inflorescence description:

*Appearance and flowering habit.*—Showy zygomorphic flowers arranged on axillary simple or branched racemes; typically three inflorescences develop per plant; each inflorescence with about eleven flowers; flowers face outwardly on upright to outwardly arching inflorescences supported by upright peduncles; flowers with three petals, two lateral petals and one center petal transformed into a labellum and three sepals.

*Fragrance.*—None detected.

*Time to flower.*—Plants begin flowering about four months after planting; plants flower naturally during the winter into the spring.

*Flower longevity*.—Long flowering period, individual inflorescences maintain good substance for about 21 weeks on the plant; flowers not persistent.

*Inflorescence length* (*lowermost flower to inflorescence apex*).—About 28.4 cm.

*Inflorescence width*.—About 16.3 cm.

*Flower buds*.—Height: About 2.2 cm. Diameter: About 1.6 cm by 1.8 cm. Shape: Broadly ovate. Color: Close to 145B; main vein, distally, close to 152D.

*Flower size*.—About 8.5 cm (vertical) by 9.3 cm (horizontal).

*Flower depth*.—About 3.1 cm.

*Petals, quantity and arrangement*.—Three, two lateral petals and one center petal transformed into a labellum.

*Lateral petals*.—Length: About 4.5 cm. Width: About 5.8 cm. Shape: Broadly reniform to close to broadly lunate. Apex: Rounded to shallowly retuse. Margin: Entire; not undulate. Texture and luster, upper and lower surfaces: Smooth, glabrous; moderately velvety; matte. Color: When opening, upper surface: Close to 157C and 157D; towards the apex and margins, close to NN155D. When opening, lower surface: Close to 157B; towards the apex and margins, close to NN155B; towards the base, close to a blend of 145D and 150D. Fully opened, upper and lower surfaces: Close to NN155D; color does not change with subsequent development.

*Labella*.—Appearance: Three-parted with two lateral lobes and a central lobe; overall shape, broadly cordate. Length, lateral lobes: About 2.2 cm. Width, lateral lobes: About 1.7 cm. Length, central lobe: About 2.1 cm. Width, central lobe: About 7 mm to 26 mm. Length, cirrhose tips: About 1.8 cm. Shape, lateral lobes: Obovate. Shape, central lobe: Kite-shaped with an elongated apex. Apex, lateral lobes: Obtuse. Apex, central lobe: Acute with two cirrhose apices, slightly moderately curled and pointing upwards and backwards. Margins, lateral and central lobes: Entire. Texture and luster, lateral and central lobes, upper and lower surfaces: Smooth, glabrous; velvety; matte. Callosities: Located at the base of the labellum and attachment point of the lateral petals; about 5 mm in length, about 6 mm in width and about 6 mm in height. Color: When opening, upper surface: Lateral lobes: Close to NN155D; at the base, axial stripes, close to 186A; lower margins, close to 154B and 154C. Central lobe: Close to NN155D; towards the base, close to 150B; at the base, close to 157C and 157D with radial stripes, close to 184C and 184D; main vein, close to 157C and 157D; cirrhose apices, close to 157C and 157D. Callosities: Close to between 1D and 155C; towards the apex, close to 1B with fine dots, close to 175A. When opening, lower surface: Lateral lobes: Close to NN155D; lower margins, close to 154B and 154C. Central lobe: Close to NN155D; towards the base, close to 151C; at the base, close to 157A and 157B; main vein, close to 150D; cirrhose apices, close to 150D. Fully opened, upper surface: Lateral lobes: Close to NN155D; at the base, axial stripes, close to 186B; lower margins, close to 2B. Central lobe: Close to NN155D; towards the base, close to 154C; at the base, close to 157C and 157D with radial stripes, close to 184C and 184D; cirrhose apices, close to 155A. Callosities: Close to between 1C and 155C; towards the apex, close to 1A with fine dots, close to 176A. Fully opened, lower surface: Lateral lobes: Close to NN155D; lower margins, close to 2B. Central lobe: Close to NN155D; towards the base, close to 151D; at the base, close to 156D; narrow marginal edges, close to 152A; main vein, close to 155C; cirrhose apices, close to 150D.

*Sepals*.—Quantity and arrangement: Three, one upper dorsal sepal and two lower lateral sepals. Length, dorsal sepal: About 4.4 cm. Width, dorsal sepal: About 3.4 cm. Length, lateral sepals: About 4.7 cm. Width, lateral sepals: About 2.7 cm. Shape, dorsal sepal: Broadly ovate-oblong to broadly oblong. Shape, lateral sepals: Ovate. Apex, dorsal sepal: Minutely and shallowly retuse. Apex, lateral sepals: Bluntly acute. Base, dorsal and lateral sepals: Cuneate. Margins, dorsal and lateral sepals: Entire; not undulate. Texture and luster, dorsal and lateral sepals, upper surface: Smooth, glabrous; velvety; matte. Texture and luster, dorsal and lateral sepals, lower surface: Smooth, glabrous; moderately velvety; matte. Color, dorsal sepal: When opening, upper surface: Close to 157C and 157D; towards the apex and margins, close to 155C. When opening, lower surface: Close to 145C; towards the margins, close to 155B and 155C; slightly tinged with close to 186D. Fully opened, upper surface: Close to NN155C and NN155D. Fully opened, lower surface: Close to NN155D; slightly tinged with close to 186D. Color, lateral sepals: When opening, upper surface: Close to 157B and 157C; towards the base, close to 145C and 145D. When opening, lower surface: Close to 145C; towards the margins, close to 155B and 155C. Fully opened, upper surface: Close to NN155C; towards the apex and margins, close to NN155D; towards the base, close to a blend of 145D and 150D. Fully opened, lower surface: Close to NN155C; towards the apex and margins, close to NN155D; towards the base, close to a blend of 145D and 150D; main vein, distally, slightly tinged with close to 186D.

*Peduncles*.—Length: About 62.8 cm. Diameter: About 6 mm. Strength: Strong. Aspect: Upright to outwardly arching. Texture and luster: Smooth, glabrous; matte. Color: Close to 137A; densely covered with fine dots and marbling, close to 147C and 147D.

*Pedicels*.—Length: About 4 cm. Diameter: About 3 mm. Strength: Moderately strong. Aspect: About 65° from peduncle axis. Texture and luster: Smooth, glabrous; matte. Color: Close to 145A; distal end, close to 145D; proximal end, close to 144B.

*Reproductive organs*.—Androecium: Column length: About 8 mm. Column width: About 6 mm. Column color: Close to NN155C. Pollinia quantity: Two. Pollinia diameter (per two pollinia): About 2.5 mm. Pollinia color: Close to 23A. Gynoecium: Stigma length: About 3 mm. Stigma width: About 4 mm. Stigma shape: Reniform. Stigma color: Close to 155C. Ovary length: About 7 mm. Ovary diameter: About 1 mm. Ovary color: Close to 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA801803' as herein illustrated and described.

* * * * *